United States Patent
Al-Daous et al.

(10) Patent No.: US 11,780,788 B2
(45) Date of Patent: Oct. 10, 2023

(54) LITHIUM-MODIFIED ZEOLITE CATALYST FOR ALKANE CRACKING

(71) Applicant: Saudi Arabian Oil Company, Dhahran (SA)

(72) Inventors: Mohammed Abdulmajeed Al-Daous, Thuwal (SA); Hussam A. Bahlouli, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/473,108

(22) Filed: Sep. 13, 2021

(65) Prior Publication Data

US 2023/0084430 A1 Mar. 16, 2023

(51) Int. Cl.
| | |
|---|---|
| C07C 4/06 | (2006.01) |
| B01J 29/40 | (2006.01) |
| B01J 29/06 | (2006.01) |
| B01J 19/24 | (2006.01) |
| B01J 8/02 | (2006.01) |

(52) U.S. Cl.
CPC .............. C07C 4/06 (2013.01); B01J 8/02 (2013.01); B01J 19/2465 (2013.01); B01J 29/061 (2013.01); B01J 29/40 (2013.01); B01J 2229/18 (2013.01); C07C 2529/40 (2013.01)

(58) Field of Classification Search
None
See application file for complete search history.

(56) References Cited

U.S. PATENT DOCUMENTS

| | | | | |
|---|---|---|---|---|
| 4,257,872 A * | 3/1981 | La Pierre | ............... | C10G 65/12 |
| | | | | 208/111.3 |
| 6,307,117 B1 * | 10/2001 | Tsunoda | .................... | C07C 4/06 |
| | | | | 585/653 |
| 7,863,212 B2 | 1/2011 | Wakui | | |
| 8,889,076 B2 * | 11/2014 | Mehlberg | ................ | C07C 4/06 |
| | | | | 422/142 |
| 2006/0116544 A1 | 6/2006 | Wakui et al. | | |
| 2021/0261417 A1* | 8/2021 | Cardinal | ................ | C01B 32/00 |

FOREIGN PATENT DOCUMENTS

| | | | | |
|---|---|---|---|---|
| WO | 2011143084 A1 | 11/2011 | | |
| WO | WO-2015137974 A1 * | 9/2015 | ............ | B01J 19/002 |
| WO | WO-2019162393 A1 * | 8/2019 | ............... | C07C 4/06 |

OTHER PUBLICATIONS

Cheung et al., "Protolytic cracking of low-molecular-weight alkanes in the presence of iron—and manganese—promoted sulfated zirconia: evidence of a compensation effect", Chemical Engineering Science, vol. 52, No. 24, pp. 4607-4613, 1997.
Jiang et al., "Highly effective P-modified HZSM-5 catalyst for the cracking of C4 alkanes to produce light olefins", Applied Catalysis A: General, vol. 340, pp. 176-182, 2008.
Lu et al., "FeHZSM-5 molecular sieves—Highly active catalysts for catalytic cracking of isobutane to produce ethylene and propylene", Catalysis Communications, vol. 7, pp. 199-203, 2006.
Lu et al., "Catalytic cracking of isobutane over HZSM-5, FeHZSM-5 and CrHZSM-5 catalysts with different SiO2/Al2O3 ratios", J. Porous Mater, vol. 15, pp. 213-220, 2008.
Maia et al., "Isobutane and n-butane cracking on Ni-ZSM-5 catalyst: Effect on light olefin formation", Applied Catalysis A: General, vol. 403, pp. 58-64, 2011.
Ono et al., "Transformation of Butanes over ZSM-5 Zeolites", J. Chem. Soc. Faraday Trans., vol. 87, No. 4, pp. 663-667, 1991.
Wakui et al., "Catalytic cracking of n-butane over rare earth—loaded HZSM-5 catalysts", Porous Materials in Environmentally Friendly Prodcesses Studies in Surface Science and Catalysis, vol. 125, 1999.
Wakui et al., "Dehydrogenative cracking of n-butane over modified HZSM-5 catalysts", Catalysis Letters, vol. 81, No. 1-2, Jul. 2002.

* cited by examiner

Primary Examiner — In Suk C Bullock
Assistant Examiner — Alyssa L Cepluch
(74) Attorney, Agent, or Firm — DINSMORE & SHOHL LLP

(57) ABSTRACT

Methods for cracking a hydrocarbon feed stream include contacting a hydrocarbon feed stream with a catalyst system in a catalytic cracking unit having a flowing gas stream to obtain a cracking product containing light olefins. The catalyst system includes at least a base catalyst. The base catalyst includes a pentasil zeolite. The pentasil zeolite includes from 0.01% to 5% by mass lithium atoms, as calculated on an oxide basis, based on the total mass of the pentasil zeolite. The flowing gas stream comprises hydrogen and, optionally, at least one additional carrier gas.

16 Claims, No Drawings

LITHIUM-MODIFIED ZEOLITE CATALYST FOR ALKANE CRACKING

TECHNICAL FIELD

This application relates to zeolite catalysts for cracking of light alkanes and to methods for cracking of light alkanes in the presence of the zeolite catalysts.

BACKGROUND

Light olefins (ethylene, propylene, and butenes) and light mono-aromatics BTX (benzene, toluene, and xylenes) are the main building blocks of the petrochemical industry that supply hundreds of millions of metric tons of manufactured raw materials every year to many chemical industries including pharmaceuticals, plastics, optics, food, and dyes. More than 70% of the ethylene produced worldwide is used to produce polyethylene. Propylene is also a building block of many chemicals, with around 67% being used to produce polypropylene.

There are different types of processes commercially available that can produce light olefins. Fluid catalytic cracking (FCC) of naphtha, or gas-oil is the main method for producing propylene, with the sum of FCC and steam cracker accounting for around 90% of the global propylene supply. Ethylene, on the other hand, is produced mainly through steam cracking of ethane, naphtha, or gas-oil. Catalytic conversion of more abundant $C_4$-$C_6$ hydrocarbons offers an alternative to produce light olefins.

SUMMARY

Against the foregoing background, ongoing needs remain for catalysts having industrially practical activity, stability, and selectivity characteristics for cracking of $C_4$-$C_6$ hydrocarbons to produce light olefins and for cracking methods incorporating the catalysts.

Accordingly, embodiments of this disclosure are directed to methods for cracking a hydrocarbon feed stream. The methods include contacting the hydrocarbon feed stream with a catalyst system in a catalytic cracking unit having a flowing gas stream to obtain a cracking product containing light olefins. The catalyst system includes a pentasil zeolite. The pentasil zeolite includes from 0.01% to 5% by mass lithium atoms, as calculated on an oxide basis, based on the total mass of the pentasil zeolite. The flowing gas stream includes hydrogen and, optionally, at least one carrier gas.

Additional features and advantages of the embodiments described herein will be set forth in the detailed description that follows, and in part will be readily apparent to those skilled in the art from that description or recognized by practicing the embodiments described herein, including the detailed description that follows, the claims, as well as the appended drawings.

It is to be understood that both the foregoing general description and the following detailed description describe various embodiments and are intended to provide an overview or framework for understanding the nature and character of the claimed subject matter.

DETAILED DESCRIPTION

Reference will be made now in detail to embodiments of methods for cracking a hydrocarbon feed stream. The methods include contacting a hydrocarbon feed stream with a catalyst system in a catalytic cracking unit having a flowing gas stream to obtain a cracking product containing light olefins. The catalyst system includes at least a base catalyst. The base catalyst includes a pentasil zeolite. The pentasil zeolite comprises from 0.01% to 5% by mass lithium atoms, as calculated on an oxide basis, based on the total mass of the pentasil zeolite. The catalyst system optionally may include other ingredients such as a catalyst additive, a catalyst matrix support, a binder, a filler, or combinations of these. The flowing gas stream comprises hydrogen and, optionally, at least one additional carrier gas.

As used in this disclosure, "cracking" generally refers to a chemical reaction by which a molecule having carbon-to-carbon bonds is broken into more than one molecule by the breaking of one or more of the carbon-to-carbon bonds, or is converted from a compound that includes a cyclic component to a compound that does not include a cyclic moiety or contains fewer cyclic moieties than prior to cracking.

As used in this disclosure, "cracking catalyst" refers to any substance that increases the rate of a cracking chemical reaction. Though cracking catalysts promote cracking of a reactant, cracking catalysts are not necessarily limited to cracking functionality and may be operable to promote other reactions.

As used in this disclosure, the term "hydrocarbon feed stream" refers to any gas or liquid fluid stream containing hydrocarbon compounds, at least a portion of which hydrocarbon compounds are saturated hydrocarbons having from four to six carbon atoms as a reactant source for a cracking reaction to produce light olefins.

As used in this disclosure, the term "light olefins" refers to unsaturated hydrocarbons having from two to four carbon atoms. Light olefins include ethylene, propylene, 1-butene, cis-2-butene, trans-2-butene, and butadiene.

As used in this disclosure, the term "pentasil zeolite" includes aluminosilicate zeolites composed of pentasil units that are linked by oxygen bridges to form pentasil chains. Pentasil units consist of eight five-membered rings. Pentasil zeolites include zeolites of family mordenite framework inverted (MFI) including, but not limited to, ZSM-5.

ZSM-5 is an aluminosilicate zeolite of the pentasil MFI family. ZSM-5 and has a nominal chemical formula of $Na_nAl_nSi_{96-n}O_{192} \cdot 16H_2O$, where subscript n is from 0 to 27. The subscript n in the ZSM-5 thus indicates a silica-to-alumina ratio (SAR) of the zeolite. ZSM-5 zeolites may be produced having silica-to-alumina ratios as small as 12 and as large as approaching infinity if nearly all of the aluminum atoms are replaced by silicon. Cations such as alkali metals in the given formula for ZSM-5 maintain charge neutrality of the zeolite. The cations may be replaced with other monovalent or divalent cations.

A successful cracking catalyst generally satisfies three requirements, namely, high activity, high selectivity, and good stability. Activity is a measure of the catalyst's ability to convert reactants into products at specified temperature, pressure, contact time, and presence of diluents such as hydrogen, steam, nitrogen, or a combination of these. Selectivity is determined with respect to a certain desired product such as light olefins or aromatic compound. Quantitatively, selectivity may be assessed as a ratio of the total amount of the desired products to the total moles of paraffin reactant converted. Stability is a measure of the rate of change with time of the activity and selectivity parameters. Smaller rates of change with time imply more stable catalysts.

The catalyst systems of the methods for cracking a hydrocarbon stream are tailored to increase selectivity for light olefins such as ethylene, propylene, and butenes, while reducing selectivity for undesired side products, particularly when catalytically cracking saturated $C_4$-$C_6$ hydrocarbons. Catalytic cracking of saturated hydrocarbons in general is a complicated reaction that is not normally selective to the production of a particular desired product. Numerous side products may form from reactions that occur along with the main cracking reaction. The side reactions may include, for example, dehydrogenation, aromatization, and hydrogen (hydride) transfer. Zeolite catalysts play an important role in converting $C_4$-$C_6$ fractions to light olefins. The porous structure and acidity of zeolites are connected to their catalytic performance in cracking reactions. ZSM-5 zeolites possess small pores and can be produced with a wide variety of silica-to-alumina ratios.

In the catalyst systems according to embodiments of this disclosure, addition of lithium to the pentasil zeolites aids in tailoring the density and strength of acid sites in the zeolites site to minimize their activity toward catalyzing undesired and competing bimolecular reactions such as aromatization and hydride transfer. Without intent to be bound by theory, it is believed that the addition of lithium to the pentasil zeolites can neutralize some of the acid sites in the zeolite structure and, depending on the amount of lithium added, the acidity of the zeolite can be fine-tuned to favor or disfavor a particular type of reaction.

The catalyst system of embodiments, including the base catalyst, will now be described in detail. The incorporation of the catalyst system in the methods for catalytic cracking of hydrocarbons will be described subsequently.

Base Catalyst

In embodiments of the methods for cracking a hydrocarbon feed stream, the catalyst system with which the hydrocarbon feed stream is contacted includes a base catalyst. The base catalyst includes a pentasil zeolite suitable for use in cracking processes. In particular, the pentasil zeolite includes from 0.01% to 5% by mass lithium atoms, as calculated on an oxide basis, based on the total mass of the pentasil zeolite. In some embodiments, the pentasil zeolite includes from 0.01% to 2% by mass lithium atoms, as calculated on an oxide basis, based on the total mass of the pentasil zeolite. In some embodiments, the pentasil zeolite includes from 0.10% to 10% by mass lithium atoms, as calculated on an oxide basis, based on the total mass of the pentasil zeolite. The pentasil zeolite may have a silica-to-alumina ratio (SAR) from 20:1 to 200:1 or from 30:1 to 100:1, or any subset of either range.

In example embodiments, the pentasil zeolite base catalyst may be ZSM-5. The ZSM-5 includes from 0.01% to 5%, or from 0.01% to 2%, or from 0.1% to 10% by mass lithium atoms, as calculated on an oxide basis, based on the total mass of the ZSM-5. The ZSM-5 may have a silica-to-alumina ratio (SAR) from 20:1 to 200:1 or from 30:1 to 100:1, or any subset of either range.

For pentasil zeolite or ZSM-5 catalysts including lithium according to some embodiments, the lithium is loaded into the catalyst by any known techniques including, but not limited to, impregnation, precipitation, or ion-exchange. For pentasil zeolite or ZSM-5 catalysts including lithium according to some embodiments, the lithium is loaded into the catalyst by ion-exchange of lithium with a counter-ion such as ammonium ($NH_4^+$) present in the ammonium form of a pentasil zeolite or ZSM-5 (for example, $NH_4^+$/ZSM-5). The lithium may be added initially from an aqueous solution of lithium or a non-aqueous solution of a lithium salt to the solid ammonium zeolite. Examples of suitable lithium salts for adding the lithium metal to the pentasil zeolite or ZSM-5 include, but are not limited to, lithium chloride or lithium chloride hydrate, lithium bromide or lithium bromide hydrate, lithium iodide or lithium iodide hydrate, lithium fluoride, lithium nitrate or lithium nitrite, lithium acetate or lithium acetate dihydrate, lithium hydroxide or lithium hydroxide monohydrate, lithium carbonate, lithium acetoacetate, lithium sulfate or lithium sulfate monohydrate, or lithium acetylacetonate. An ion-exchanged zeolite solid may be dried at 110° C. then calcined at 550° C. to 600° C. under static air to produce a pentasil zeolite or a ZSM-5 zeolite containing lithium in the form of lithium ions, $Li_2O$, or combinations thereof.

Catalytic Cracking Process

In the methods for cracking a hydrocarbon feed stream, the hydrocarbon feed stream is contacted with the catalyst system, as previously described, in a catalytic cracking unit having a flowing gas stream to obtain a cracking product containing light olefins. The cracking method including the catalyst system as an integral component will now be described in detail.

In the methods for cracking a hydrocarbon feed stream, the hydrocarbon feed stream is a gas or liquid fluid stream containing saturated hydrocarbons that have from four to six carbon atoms as a reactant source for the cracking reaction to produce light olefins such as ethylene, propylene, and butenes. Examples of saturated hydrocarbons having from four to six carbon atoms include n-butane, 2-methylpropane (iso-butane), n-pentane, 1-methylbutane, n-hexane, 2-methylpentane, 3-methylpentane, and 2,3-dimethylbutane. The hydrocarbon feed stream may be a $C_4$-$C_6$ refinery stream derived from crude oil, for example.

The flowing gas stream includes hydrogen and, optionally, at least one carrier gas. Examples of carrier gases include steam, nitrogen, argon, and combinations thereof. In some examples, the flowing gas stream includes hydrogen and nitrogen. The flowing gas stream may have a flow rate suited to the capacity and volume of the catalytic cracking unit. When the flowing gas stream includes a carrier gas in addition to the hydrogen, the volumetric flow-rate ratios of hydrogen to carrier gas in the flowing gas stream may be selected to provide a desired catalyst activity and selectivity. Without intent to be bound by theory, it is believed that the hydrogen flow rate in the catalytic cracking unit, when chosen to establish a hydrogen equilibrium over the catalyst system reduces the rates of undesired side-reactions and increases the yields of light olefins (ethylene, propylene) over aromatic compounds and prolongs catalyst stability under typical reaction conditions.

In some example embodiments, the flowing gas stream includes hydrogen and nitrogen at a volumetric flow-rate ratio $H_2$:$N_2$ from 1000:1 to 1:50. In further examples, the gas stream includes from 2% to 85% by volume hydrogen, balanced by nitrogen. Without intent to be bound by theory, it is believed that including hydrogen in the flowing gas stream stabilizes the catalyst against coke formation and facilitate continuous butane cracking in a fixed-bed based reactor for extended durations.

In the methods for cracking the hydrocarbon feed stream, the contacting of the hydrocarbon feed stream may occur at a reaction temperature from 450° C. to 700° C. of from 500° C. to 650° C.

The contacting may occur at a reaction pressure from 0.01 bar to 10 bar. For example, the reaction mixture may contact the cracking catalyst at a pressure of from 0.01 bar to 8 bar, from 0.01 bar to 6 bar, from 0.01 bar to 4 bar, from 0.01 bar to 2 bar, from 0.01 bar to 1 bar, from 0.1 bar to 8 bar, from 0.1 bar to 6 bar, from 0.1 bar to 4 bar, from 0.1 bar to 2 bar, from 0.1 bar to 1 bar, from 1 bar to 10 bar, from 1 bar to 8 bar, from 1 bar to 6 bar, from 1 bar to 4 bar, from 1 bar to 2 bar, from 2 bar to 8 bar, from 2 bar to 6 bar, from 2 bar to 4 bar, or any subset thereof.

The contacting may occur with a residence or contact time from 0.1 seconds to 60 seconds. The contacting may occur with a weight hour space velocity (WHSV) from 0.5 per hour ($h^{-1}$) to 4 $h^{-1}$. For example, the WHSV may be from 1 $h^{-1}$ to 4 $h^{-1}$, from 2 $h^{-1}$ to 4 $h^{-1}$, from 3 $h^{-1}$ to 4 $h^{-1}$, from 0.5 $h^{-1}$ to 3 $h^{-1}$, from 0.5 $h^{-1}$ to 2 $h^{-1}$, from 0.5 $h^{-1}$ to 1 $h^{-1}$, from 1 $h^{-1}$ to 3 $h^{-1}$, or any subset thereof. WHSV is calculated as the feed rate divided by the weight of catalyst. For example, for a feed of 2 kilograms per hour (kg/h) hydrocarbon and 1 kg cracking catalyst, the WHSV would be 2 per hour. The contacting may occur with a catalyst to oil ratio from about 2:1 to 30:1. Without intent to be bound by theory, it is believed that to achieve high conversion in $C_4$-$C_6$ cracking, high reaction temperature and low alkane partial pressure are desirable.

The cracking product of the methods for cracking a hydrocarbon feed stream include ethylene, propylene, and butylenes. The cracking product may further include saturated and unsaturated hydrocarbons, aromatics (particularly benzene, toluene, and xylenes), hydrogen, and carrier gas, if used. In some embodiments, the methods may further include recovering hydrogen from the cracking product. The hydrogen so-obtained may be utilized elsewhere or recycled to the process. In some embodiments, the methods may include further separating from the cracking product a first liquid stream including hydrocarbons with four or fewer hydrogen atoms, a second stream rich in saturated hydrocarbons, and a third stream rich in unsaturated hydrocarbons. The separated unconverted saturated hydrocarbons of the third stream may then be recycled along with the $C_4$-$C_9$ olefins. The separation can be performed in any conventional manner, such as but not limited to simple gas-liquid separation.

EXAMPLES

The following examples are offered by way of illustration and in a manner such that one skilled in the art will recognize is not meant to be limiting to the scope of the present disclosure or its claims.

Examples 1-12 describe the synthesis of twelve ZSM-5 zeolites included as the catalyst system for cracking reactions of a hydrocarbon feed stream. Three series of four ZSM-5 samples were prepared. The three series were made according to silica to alumina ratios ($SiO_2/Al_2O_3$) of 23 (Examples 1-4), 50 (Examples 5-8), and 80 (Examples 9-12). In each series, the four samples had nominal lithium mass percent of zero (Examples 1, 5, and 9), 0.14% (Examples 2, 6, and 10), 0.35% (Examples 3, 7, and 11), and 0.69% (Examples 4, 8, and 12). Thus, the ZSM-5 zeolites of Examples 1, 5, and 9 with no lithium were comparative control samples for their respective series.

The twelve catalysts were evaluated for performance in cracking reactions in a fixed-bed reactor, to which a hydrocarbon feed stream containing 5% to 20% by volume butane feed balanced with a carrier gas mixture. The butane feed consisted of 30% iso-butane and 70% n-butane by volume. The carrier gas mixture contained hydrogen in one trial and a mixture of hydrogen and nitrogen in the remaining four trials, at flow-rate ratios $H_2/N_2$ of 50:23, 30:43, 10:63, and 2:72. The lithium-modified catalysts and the reaction conditions produced light olefins (ethylene, propylene and butylenes) with reduced yields of aromatics, methane, and hydride-transfer reaction products such ethane and propane as compared to the controls, and with catalyst stabilization from the hydrogen that prevented deactivation from coke formation.

Example 1 (Comparative)

Preparation of Catalyst A: ZSM-5(23)

Commercial ZSM-5 zeolite with $SiO_2/Al_2O_3$ of 23 supplied by Alfa Aesar (ammonium form, $NH_4^+$/ZSM-5). The active form of the zeolite catalyst was obtained by calcining the received ammonium form using the following thermal treatment regime, under static air: Initial temperature 25° C., heat at 5° C./minute to 120° C., hold for 3 hours, heat at 2° C./minute to 600° C., hold for 7 hours. The obtained calcined product is denoted as ZSM-5(23).

Example 2

Preparation of Catalyst B: 0.01MLi/ZSM-5(23)

Commercial ZSM-5 zeolite with $SiO_2/Al_2O_3$ of 23 supplied by Alfa Aesar (ammonium form, $NH_4^+$/ZSM-5). A total of 25 grams of the zeolite was dispersed in 1-liter solution of 0.01-M $Li(NO_3)$ (lithium nitrate) and stirred at 80° C. for 6 hours. The dispersion was allowed to cool to room temperature before separating the solid by filtration. The solid zeolite was dried at 100° C. for 16 hours prior to calcination using the following thermal treatment regime, under static air: Initial temperature 25° C., heat at 5° C./minute to 120° C., hold for 3 hours, heat at 2° C./minute to 600° C., hold for 7 hours. The obtained calcined product is denoted as 0.01MLi/ZSM-5(23). The nominal amount of lithium in the product was 0.14% by mass, based on the total mass of the product.

Example 3

Preparation of Catalyst C: 0.025MLi/ZSM-5(23)

Commercial ZSM-5 zeolite with $SiO_2/Al_2O_3$ of 23 supplied by Alfa Aesar (ammonium form, $NH_4^+$/ZSM-5). A total of 25 grams of the zeolite was dispersed in 1-liter solution of 0.025-M $Li(NO_3)$ (lithium nitrate) and stirred at 80° C. for 6 hours. The dispersion was allowed to cool to room temperature before separating the solid by filtration. The solid zeolite was dried at 100° C. for 16 hours prior to calcination using the following thermal treatment regime, under static air: Initial temperature 25° C., heat at 5° C./minute to 120° C., hold for 3 hours, heat at 2° C./minute to 600° C., hold for 7 hours. The obtained calcined product is denoted as 0.025MLi/ZSM-5(23). The nominal amount of lithium in the product was 0.35% by mass, based on the total mass of the product.

Example 4

Preparation of Catalyst D: 0.05MLi/ZSM-5(23)

Commercial ZSM-5 zeolite with $SiO_2/Al_2O_3$ of 23 supplied by Alfa Aesar (ammonium form, $NH_4^+$/ZSM-5). A total of 25 grams of the zeolite was dispersed in 1-liter solution of 0.05-M $Li(NO_3)$ (lithium nitrate) and stirred at 80° C. for 6 hours. The dispersion was allowed to cool to room temperature before separating the solid by filtration. The solid zeolite was dried at 100° C. for 16 hours prior to calcination using the following thermal treatment regime, under static air: Initial temperature 25° C., heat at 5° C./minute to 120° C., hold for 3 hours, heat at 2° C./minute to 600° C., hold for 7 hours. The obtained calcined product is denoted as 0.05MLi/ZSM-5(23). The nominal amount of lithium in the product was 0.69% by mass, based on the total mass of the product.

Example 5 (Comparative)

Preparation of Catalyst E: ZSM-5(50)

Commercial ZSM-5 zeolite with $SiO_2/Al_2O_3$ of 50 supplied by Alfa Aesar (ammonium form, $NH_4^+$/ZSM-5). The active form of the zeolite catalyst was obtained by calcining the received ammonium form using the following thermal treatment regime, under static air: Initial temperature 25° C., heat at 5° C./minute to 120° C., hold for 3 hours, heat at 2° C./minute to 600° C., hold for 7 hours. The obtained calcined product is denoted as ZSM-5(50).

Example 6

Preparation of Catalyst F: 0.01MLi/ZSM-5(50)

Commercial ZSM-5 zeolite with $SiO_2/Al_2O_3$ of 50 supplied by Alfa Aesar (ammonium form, $NH_4^+$/ZSM-5). A total of 25 grams of the zeolite was dispersed in a 1-liter solution of 0.01-M $Li(NO_3)$ (lithium nitrate) and stirred at 80° C. for 6 hours. The dispersion was allowed to cool to room temperature before separating the solid by filtration. The solid zeolite was dried at 100° C. for 16 hours prior to calcination using the following thermal treatment regime, under static air: Initial temperature 25° C., heat at 5° C./minute to 120° C., hold for 3 hours, heat at 2° C./minute to 600° C., hold for 7 hours. The obtained calcined product is denoted as 0.01MLi/ZSM-5(50). The nominal amount of lithium in the product was 0.14% by mass, based on the total mass of the product.

Example 7

Preparation of Catalyst G: 0.025MLi/ZSM-5(50)

Commercial ZSM-5 zeolite with $SiO_2/Al_2O_3$ of 50 supplied by Alfa Aesar (ammonium form, $NH_4^+$/ZSM-5). A total of 25 grams of the zeolite was dispersed in 1-liter solution of 0.025-M $Li(NO_3)$ (lithium nitrate) and stirred at 80° C. for 6 hours. The dispersion was allowed to cool to room temperature before separating the solid by filtration. The solid zeolite was dried at 100° C. for 16 hours prior to calcination using the following thermal treatment regime, under static air: Initial temperature 25° C., heat at 5° C./minute to 120° C., hold for 3 hours, heat at 2° C./minute to 600° C., hold for 7 hours. The obtained calcined product is denoted as 0.025MLi/ZSM-5(50). The nominal amount of lithium in the product was 0.35% by mass, based on the total mass of the product.

Example 8

Preparation of Catalyst H: 0.05MLi/ZSM-5(50)

Commercial ZSM-5 zeolite with $SiO_2/Al_2O_3$ of 50 supplied by Alfa Aesar (ammonium form, $NH_4^+$/ZSM-5). A total of 25 grams of the zeolite was dispersed in 1-liter solution of 0.05-M $Li(NO_3)$ (lithium nitrate) and stirred at 80° C. for 6 hours. The dispersion was allowed to cool to room temperature before separating the solid by filtration. The solid zeolite was dried at 100° C. for 16 hours prior to calcination using the following thermal treatment regime, under static air: Initial temperature 25° C., heat at 5° C./minute to 120° C., hold for 3 hours, heat at 2° C./minute to 600° C., hold for 7 hours. The obtained calcined product is denoted as 0.05MLi/ZSM-5(50). The nominal amount of lithium in the product was 0.69% by mass, based on the total mass of the product.

Example 9 (Comparative)

Preparation of Catalyst I: ZSM-5(80)

Commercial ZSM-5 zeolite with $SiO_2/Al_2O_3$ of 80 supplied by Zeolyst (ammonium form, $NH_4^+$/ZSM-5). The active form of the zeolite catalyst was obtained by calcining the received ammonium form using the following thermal treatment regime, under static air: Initial temperature 25° C., heat at 5° C./minute to 120° C., hold for 3 hours, heat at 2° C./minute to 600° C., hold for 7 hours. The obtained calcined product is denoted as ZSM-5(80).

Example 10

Preparation of Catalyst J: 0.01MLi/ZSM-5(80)

Commercial ZSM-5 zeolite with $SiO_2/Al_2O_3$ of 80 supplied by Zeolyst (ammonium form, $NH_4^+$/ZSM-5). A total of 25 grams of the zeolite was dispersed in 1-liter solution of 0.01-M $Li(NO_3)$ (lithium nitrate) and stirred at 80° C. for 6 hours. The dispersion was allowed to cool to room temperature before separating the solid by filtration. The solid zeolite was dried at 100° C. for 16 hours prior to calcination using the following thermal treatment regime, under static air: Initial temperature 25° C., heat at 5° C./minute to 120° C., hold for 3 hours, heat at 2° C./minute to 600° C., hold for 7 hours. The obtained calcined product is denoted as 0.01MLi/ZSM-5(80). The nominal amount of lithium in the product was 0.14% by mass, based on the total mass of the product.

Example 11

Preparation of Catalyst K: 0.025MLi/ZSM-5(80)

Commercial ZSM-5 zeolite with $SiO_2/Al_2O_3$ of 80 supplied by Zeolyst (ammonium form, $NH_4^+$/ZSM-5). A total of 25 grams of the zeolite was dispersed in 1-liter solution of 0.025-M $Li(NO_3)$ (lithium nitrate) and stirred at 80° C. for 6 hours. The dispersion was allowed to cool to room temperature before separating the solid by filtration. The solid zeolite was dried at 100° C. for 16 hours prior to calcination using the following thermal treatment regime, under static air: Initial temperature 25° C., heat at 5° C./minute to 120° C., hold for 3 hours, heat at 2° C./minute to 600° C., hold for 7 hours. The obtained calcined product is denoted as 0.025MLi/ZSM-5(80). The nominal amount of lithium in the product was 0.35% by mass, based on the total mass of the product.

Example 12

Preparation of Catalyst L: 0.05MLi/ZSM-5(80)

Commercial ZSM-5 zeolite with $SiO_2/Al_2O_3$ of 80 supplied by Zeolyst (ammonium form, $NH_4^+$/ZSM-5). A total of 25 grams of the zeolite was dispersed in 1-liter solution of 0.05-M $Li(NO_3)$ (lithium nitrate) and stirred at 80° C. for 6 hours. The dispersion was allowed to cool to room temperature before separating the solid by filtration. The solid zeolite was dried at 100° C. for 16 hours prior to calcination using the following thermal treatment regime, under static air: Initial temperature 25° C., heat at 5° C./minute to 120° C., hold for 3 hours, heat at 2° C./minute to 600° C., hold for 7 hours. The obtained calcined product is denoted as 0.05MLi/ZSM-5(80). The nominal amount of lithium in the product was 0.69% by mass, based on the total mass of the product.

Example 13

Catalysts Treatment and Activation

Catalysts were tested in fixed-bed reactor. The catalysts as prepared in the examples were pressed at 8 tons (7250 kg) pressure to form tablets and were crushed and sieved to form 200 to 500 micrometer granules. The granules (approx. 1.0 cm³, 0.5 grams) were packed into a tubular Hastelloy-X reactor that was 510 millimeters in length and with 5 millimeters internal diameter. The reactor had a thermocouple immersed into the catalyst bed.

A gas mixture of nitrogen (about 70 cm³/min) and hydrogen (about 10 cm³/min) was passed over the catalyst, and the temperature was raised to 600° C. at the rate of 5° C./min and kept at 600° C. for at least 30 minutes. The temperature then was changed to the reaction temperature of 650° C. at a rate of 5° C./min.

Example 14

Catalysts Testing in Butane Cracking

Catalysts were used for butane (30% iso-butane and 70% n-butane) cracking reaction to produce lower olefins (ethylene, propylene and butylene) along with propane, ethane, methane and aromatics as the main side products. Activity values listed in Tables 1-11 were measured after 4 hours on stream with weight hour space velocity (WHSV) of 2 h- and 0.5 grams of catalyst at reaction temperature of 650° C. and under atmospheric pressure. The feed stream contained 12.5 volume percent butane (30% iso-butane and 70% n-butane) and diluted with a carrier gas made of a mixture of hydrogen and nitrogen with the composition ratios listed in the tables.

Activity of butane cracking reactions over the various catalysts of the foregoing Examples is summarized in the following Tables 1-11. Tables 1-6 provide the activity data for individual catalysts at all tested $H_2/N_2$ ratios to illustrate performance characteristics of the individual catalysts with varying of the $H_2/N_2$ ratio. Tables 7-11 provide the same activity data as Tables 1-6, rearranged to show the performance characteristics of all catalysts A-L for butane cracking at the same $H_2/N_2$ ratio. In all of Tables 1-11, "Butanes" refers to the total of iso-butane and n-butane; "Butenes" refers to the total of 1-butene, cis-2-butene, trans-2-butene, and butadiene; and "Aromatics" refers to the total of all BTX compounds, namely, benzene, toluene, and xylenes (p-xylene, m-xylene, and o-xylene). In all of Tables 1-11, "(E+B+P)" is the sum of the product distribution amounts of ethylene, butenes, and propylene, and "(E+B+P)/A" the sum of the product distribution amounts of ethylene, butenes, and propylene, divided by the product distribution amount of aromatics. In all of Tables 1-11, the row "Vs. Control" is the (E+B+P)/A value for the particular catalyst, divided by the (E+B+P)/A value for the control catalyst (Catalyst A, Catalyst E, or Catalyst I) having the same $SiO_2/Al_2O_3$ ratio and no lithium.

TABLE 1

Activity of butane cracking over catalysts A and B

| | Catalyst A (Comparative) | | | | | Catalyst B | | | | |
|---|---|---|---|---|---|---|---|---|---|---|
| | | | | | $SiO_2/Al_2O_3$ | | | | | |
| | 23 | | | | | 23 | | | | |
| | | | | | Li (mass %) | | | | | |
| | 0 | | | | | 0.14% | | | | |
| | | | | | $H_2:N_2$, (mL/min) | | | | | |
| | 74:0 | 50:23 | 30:43 | 10:63 | 2:72 | 74:0 | 50:23 | 30:43 | 10:63 | 2:72 |
| | | | | | conversion | | | | | |
| | 99.0% | 99.0% | 99.0% | 99.4% | 99.8% | 99.6% | 99.6% | 99.6% | 99.6% | 99.7% |
| | Product Distribution mole/100 mole | | | | | Product Distribution mole/100 mole | | | | |
| Butanes | 1.0 | 1.0 | 1.0 | 0.6 | 0.2 | 0.4 | 0.4 | 0.4 | 0.4 | 0.3 |
| Butenes | 1.2 | 1.3 | 1.4 | 1.1 | 0.7 | 0.9 | 1.0 | 1.0 | 0.8 | 0.6 |
| Ethylene | 22.5 | 22.5 | 24.1 | 22.0 | 19.3 | 25.5 | 22.7 | 20.7 | 17.7 | 15.1 |
| Propylene | 10.5 | 10.9 | 11.5 | 9.8 | 7.1 | 9.1 | 8.9 | 8.6 | 7.3 | 5.8 |
| Propane | 4.6 | 4.1 | 3.3 | 2.6 | 2.4 | 4.0 | 3.1 | 2.5 | 1.8 | 1.7 |
| Ethane | 11.6 | 9.3 | 9.3 | 6.1 | 5.4 | 14.0 | 11.0 | 9.3 | 7.3 | 5.8 |
| Methane | 16.3 | 15.1 | 13.9 | 12.7 | 12.9 | 19.1 | 15.3 | 13.1 | 11.2 | 10.2 |
| iso-Olefins | 0.6 | 0.6 | 0.6 | 0.5 | 0.3 | 0.5 | 0.5 | 0.5 | 0.4 | 0.3 |
| Aromatics | 31.7 | 33.9 | 34.9 | 43.2 | 51.1 | 26.4 | 37.2 | 43.9 | 53.2 | 60.3 |
| (E + B + P) | 34.0 | 34.4 | 36.6 | 32.4 | 26.6 | 35.0 | 32.0 | 29.7 | 25.4 | 21.2 |
| (E + B + P)/A | 1.1 | 1.0 | 1.0 | 0.8 | 0.5 | 1.3 | 0.9 | 0.7 | 0.5 | 0.4 |
| Vs. Control | 1 | 1 | 1 | 1 | 1 | 1.2 | 0.9 | 0.7 | 0.6 | 0.7 |

TABLE 2

Activity of butane cracking over catalysts C and D

| | Catalyst C | | | | | Catalyst D | | | | |
|---|---|---|---|---|---|---|---|---|---|---|
| | $SiO_2/Al_2O_3$ | | | | | | | | | |
| | 23 | | | | | 23 | | | | |
| | Li (mass %) | | | | | | | | | |
| | 0.35% | | | | | 0.69% | | | | |
| | $H_2:N_2$, (mL/min) | | | | | | | | | |
| | 74:0 | 50:23 | 30:43 | 10:63 | 2:72 | 74:0 | 50:23 | 30:43 | 10:63 | 2:72 |
| | conversion | | | | | | | | | |
| | 97.6% | 97.3% | 96.8% | 97.2% | 98.3% | 84.8% | 84.2% | 83.7% | 85.5% | 90.8% |
| | Product Distribution mole/100 mole | | | | | | | | | |
| Butanes | 2.4 | 2.7 | 3.2 | 2.8 | 1.7 | 15.2 | 15.8 | 16.3 | 14.5 | 9.2 |
| Butenes | 1.6 | 1.8 | 1.8 | 1.7 | 1.2 | 3.3 | 3.7 | 3.9 | 3.9 | 3.2 |
| Ethylene | 27.9 | 24.1 | 22.3 | 20.5 | 18.2 | 22.0 | 20.1 | 19.0 | 19.0 | 19.7 |
| Propylene | 14.6 | 13.8 | 13.6 | 12.3 | 9.6 | 20.1 | 19.2 | 18.6 | 17.5 | 15.3 |
| Propane | 4.6 | 3.4 | 2.6 | 2.1 | 1.8 | 3.7 | 2.8 | 2.2 | 1.7 | 1.6 |
| Ethane | 12.9 | 10.0 | 8.4 | 6.7 | 5.4 | 10.1 | 8.1 | 6.8 | 5.5 | 4.8 |
| Methane | 17.5 | 14.0 | 12.3 | 11.0 | 10.1 | 14.5 | 12.3 | 10.9 | 9.8 | 9.4 |
| iso-Olefins | 0.8 | 0.8 | 0.9 | 0.8 | 0.6 | 1.8 | 1.8 | 1.9 | 1.9 | 1.5 |
| Aromatics | 17.6 | 29.4 | 34.9 | 42.2 | 51.5 | 9.3 | 16.3 | 20.5 | 26.2 | 35.3 |
| (E + B + P) | 44.9 | 40.6 | 39.1 | 35.6 | 29.5 | 57.3 | 55.1 | 53.9 | 51.0 | 44.2 |
| (E + B + P)/A | 2.6 | 1.4 | 1.1 | 0.8 | 0.6 | 6.2 | 3.4 | 2.6 | 1.9 | 1.3 |
| Vs. Control | 2.3 | 1.3 | 1.0 | 1.1 | 1.1 | 4.5 | 2.6 | 1.9 | 2.0 | 2.0 |

TABLE 3

Activity of butane cracking over catalysts E and F

| | Catalyst E (Comparative) | | | | | Catalyst F | | | | |
|---|---|---|---|---|---|---|---|---|---|---|
| | $SiO_2/Al_2O_3$ | | | | | | | | | |
| | 50 | | | | | 50 | | | | |
| | Li (mass %) | | | | | | | | | |
| | 0 | | | | | 0.14% | | | | |
| | $H_2:N_2$, (mL/min) | | | | | | | | | |
| | 74:0 | 50:23 | 30:43 | 10:63 | 2:72 | 74:0 | 50:23 | 30:43 | 10:63 | 2:72 |
| | conversion | | | | | | | | | |
| | 99.3% | 99.2% | 99.1% | 99.5% | 99.8% | 98.1% | 98.4% | 98.5% | 98.8% | 99.3% |
| | Product Distribution mole/100 mole | | | | | Product Distribution mole/100 mole | | | | |
| Butanes | 0.7 | 0.8 | 0.9 | 0.5 | 0.2 | 1.9 | 1.6 | 1.5 | 1.2 | 0.7 |
| Butenes | 1.3 | 1.3 | 1.4 | 1.0 | 0.6 | 1.9 | 1.8 | 1.8 | 1.6 | 1.2 |
| Ethylene | 28.3 | 21.5 | 20.4 | 18.2 | 16.2 | 29.9 | 27.2 | 26.1 | 24.0 | 21.2 |
| Propylene | 12.0 | 10.7 | 10.7 | 8.8 | 6.5 | 15.8 | 14.8 | 14.6 | 13.2 | 10.4 |
| Propane | 4.7 | 3.8 | 3.5 | 2.9 | 2.5 | 5.0 | 3.8 | 3.1 | 2.5 | 2.4 |
| Ethane | 13.0 | 9.7 | 8.7 | 7.0 | 5.3 | 13.7 | 11.0 | 9.5 | 8.0 | 6.7 |
| Methane | 17.6 | 13.6 | 12.3 | 11.4 | 11.1 | 17.8 | 14.3 | 12.6 | 11.2 | 10.7 |
| iso-Olefins | 0.6 | 0.6 | 0.7 | 0.5 | 0.3 | 0.9 | 0.9 | 0.9 | 0.8 | 0.6 |
| Aromatics | 21.7 | 38.1 | 41.4 | 49.8 | 57.3 | 13.2 | 24.7 | 29.9 | 37.6 | 46.4 |
| (E + B + P) | 41.0 | 33.0 | 32.0 | 27.5 | 22.9 | 47.6 | 43.6 | 42.2 | 38.4 | 32.3 |
| (E + B + P)/A | 1.9 | 0.9 | 0.8 | 0.6 | 0.4 | 3.6 | 1.8 | 1.4 | 1.0 | 0.7 |
| Vs. Control | 1 | 1 | 1 | 1 | 1 | 1.9 | 2.0 | 1.8 | 1.8 | 1.7 |

TABLE 4

Activity of butane cracking over catalysts G and H

| | Catalyst G | | | | | Catalyst H | | | | |
|---|---|---|---|---|---|---|---|---|---|---|
| | SiO$_2$/Al$_2$O$_3$ | | | | | | | | | |
| | 50 | | | | | 50 | | | | |
| | Li (mass %) | | | | | | | | | |
| | 0.35% | | | | | 0.69% | | | | |
| | H$_2$:N$_2$, (mL/min) | | | | | | | | | |
| | 74:0 | 50:23 | 30:43 | 10:63 | 2:72 | 74:0 | 50:23 | 30:43 | 10:63 | 2:72 |
| | conversion | | | | | | | | | |
| | 94.9% | 94.4% | 94.6% | 95.2% | 96.6% | 86.8% | 84.2% | 84.1% | 85.9% | 90.2% |
| | Product Distribution mole/100 mole | | | | | Product Distribution mole/100 mole | | | | |
| Butanes | 5.1 | 5.6 | 5.4 | 4.8 | 3.4 | 13.2 | 15.8 | 15.9 | 14.1 | 9.8 |
| Butenes | 2.6 | 2.5 | 2.9 | 2.7 | 2.1 | 3.5 | 4.3 | 4.3 | 4.2 | 3.6 |
| Ethylene | 25.8 | 28.1 | 25.7 | 24.2 | 22.7 | 18.2 | 21.4 | 20.7 | 20.9 | 21.4 |
| Propylene | 17.9 | 20.1 | 19.0 | 17.6 | 15.0 | 18.1 | 21.7 | 21.5 | 20.7 | 18.4 |
| Propane | 5.0 | 3.7 | 2.9 | 2.4 | 2.3 | 2.8 | 2.8 | 2.3 | 2.1 | 2.1 |
| Ethane | 13.4 | 10.1 | 9.3 | 7.9 | 6.7 | 8.5 | 8.8 | 7.7 | 6.7 | 5.9 |
| Methane | 16.6 | 13.5 | 12.5 | 11.1 | 10.5 | 11.4 | 12.3 | 11.1 | 10.1 | 9.7 |
| iso-Olefins | 1.2 | 1.4 | 1.4 | 1.3 | 1.0 | 1.7 | 2.0 | 2.1 | 2.1 | 1.7 |
| Aromatics | 12.4 | 15.1 | 20.8 | 27.9 | 36.2 | 22.7 | 10.9 | 14.2 | 19.2 | 27.4 |
| (E + B + P) | 48.8 | 53.8 | 50.1 | 46.6 | 41.1 | 49.5 | 58.9 | 58.1 | 55.7 | 49.6 |
| (E + B + P)/A | 3.9 | 3.6 | 2.4 | 1.7 | 1.1 | 2.2 | 5.4 | 4.1 | 2.9 | 1.8 |
| Vs. Control | 1.9 | 3.8 | 2.9 | 2.8 | 2.7 | 0.9 | 4.9 | 4.2 | 4.2 | 3.9 |

TABLE 5

Activity of butane cracking over catalysts I and J

| | Catalyst I (Comparative) | | | | | Catalyst J | | | | |
|---|---|---|---|---|---|---|---|---|---|---|
| | SiO$_2$/Al$_2$O$_3$ | | | | | | | | | |
| | 80 | | | | | 80 | | | | |
| | Li (mass %) | | | | | | | | | |
| | 0 | | | | | 0.14% | | | | |
| | H$_2$:N$_2$ (mL/min) | | | | | | | | | |
| | 74:0 | 50:23 | 30:43 | 10:63 | 2:72 | 74:0 | 50:23 | 30:43 | 10:63 | 2:72 |
| | conversion | | | | | | | | | |
| | 98.0% | 97.6% | 96.2% | 95.7% | 95.8% | 89.5% | 90.2% | 89.7% | 89.3% | 89.5% |
| | Product Distribution mole/100 mole | | | | | Product Distribution mole/100 mole | | | | |
| Butanes | 2.0 | 2.4 | 3.8 | 4.3 | 4.2 | 10.5 | 9.8 | 10.3 | 10.7 | 10.5 |
| Butenes | 1.8 | 2.1 | 2.6 | 2.6 | 2.4 | 3.6 | 3.7 | 3.9 | 4.0 | 3.8 |
| Ethylene | 26.0 | 27.2 | 27.9 | 26.4 | 24.8 | 24.1 | 23.8 | 23.0 | 21.9 | 20.5 |
| Propylene | 14.7 | 16.3 | 18.5 | 18.5 | 17.2 | 20.0 | 20.7 | 21.1 | 21.0 | 19.6 |
| Propane | 4.3 | 3.7 | 3.1 | 2.7 | 2.8 | 4.4 | 3.5 | 2.8 | 2.6 | 2.6 |
| Ethane | 12.6 | 11.4 | 10.4 | 9.1 | 8.1 | 13.2 | 10.7 | 9.1 | 7.9 | 7.0 |
| Methane | 15.9 | 14.6 | 13.6 | 12.3 | 11.9 | 16.4 | 13.4 | 11.5 | 10.2 | 9.6 |
| iso-Olefins | 0.8 | 1.0 | 1.2 | 1.3 | 1.1 | 1.8 | 1.8 | 1.9 | 1.9 | 1.8 |
| Aromatics | 21.7 | 21.2 | 18.9 | 22.8 | 27.5 | 6.1 | 12.5 | 16.2 | 19.8 | 24.5 |
| (E + B + P) | 42.7 | 45.9 | 50.2 | 49.2 | 46.2 | 54.6 | 54.3 | 54.4 | 53.6 | 50.6 |
| (E + B + P)/A | 2.0 | 2.2 | 2.7 | 2.2 | 1.7 | 9.0 | 4.3 | 3.4 | 2.7 | 2.1 |
| Vs. Control | 1 | 1 | 1 | 1 | 1 | 4.0 | 1.8 | 1.1 | 1.1 | 1.1 |

TABLE 6

Activity of butane cracking over catalysts K and L

| | Catalyst K | | | | | Catalyst L | | | | |
|---|---|---|---|---|---|---|---|---|---|---|
| | $SiO_2/Al_2O_3$ | | | | | | | | | |
| | 80 | | | | | 80 | | | | |
| | Li (mass %) | | | | | | | | | |
| | 0.35% | | | | | 0.69% | | | | |
| | $H_2:N_2$, (mL/min) | | | | | | | | | |
| | 74:0 | 50:23 | 30:43 | 10:63 | 2:72 | 74:0 | 50:23 | 30:43 | 10:63 | 2:72 |
| | conversion | | | | | | | | | |
| | 75.1% | 81.0% | 80.5% | 80.9% | 81.7% | 70.9% | 71.3% | 70.1% | 70.4% | 72.0% |
| | Product Distribution mole/100 mole | | | | | Product Distribution mole/100 mole | | | | |
| Butanes | 24.9 | 19.0 | 19.5 | 19.1 | 18.3 | 29.1 | 28.7 | 29.9 | 29.6 | 28.0 |
| Butenes | 4.5 | 4.5 | 4.8 | 5.1 | 5.2 | 4.5 | 5.1 | 5.4 | 6.0 | 6.4 |
| Ethylene | 19.0 | 21.1 | 20.4 | 19.8 | 18.8 | 16.8 | 17.1 | 16.6 | 16.1 | 15.8 |
| Propylene | 15.7 | 22.0 | 22.3 | 22.6 | 21.7 | 19.4 | 20.9 | 21.1 | 21.2 | 21.0 |
| Propane | 2.9 | 2.8 | 2.4 | 2.5 | 2.7 | 2.7 | 2.2 | 1.9 | 2.0 | 2.3 |
| Ethane | 14.1 | 9.5 | 8.3 | 7.1 | 6.3 | 10.1 | 8.4 | 7.2 | 6.1 | 5.4 |
| Methane | 12.7 | 12.3 | 11.0 | 9.9 | 9.3 | 13.4 | 11.2 | 9.9 | 8.8 | 8.4 |
| iso-Olefins | 2.4 | 2.2 | 2.3 | 2.5 | 2.5 | 2.2 | 2.5 | 2.6 | 2.8 | 3.0 |
| Aromatics | 3.8 | 6.6 | 8.9 | 11.3 | 15.2 | 1.7 | 4.0 | 5.4 | 7.4 | 9.6 |
| (E + B + P) | 59.6 | 62.1 | 62.2 | 61.5 | 58.8 | 65.3 | 66.7 | 67.6 | 66.9 | 64.8 |
| (E + B + P)/A | 15.7 | 9.4 | 7.0 | 5.4 | 3.9 | 38.4 | 16.7 | 12.5 | 9.0 | 6.8 |
| Vs. Control | 5.3 | 3.4 | 2.1 | 2.0 | 1.9 | 12.2 | 5.0 | 3.1 | 2.8 | 2.8 |

TABLE 7

Activity of butane cracking over catalysts A-L at $H_2/N_2$ flow-rate ratio of 74:0

| | Catalyst | | | | | | | | | | | |
|---|---|---|---|---|---|---|---|---|---|---|---|---|
| | A* | B | C | D | E* | F | G | H | I* | J | K | L |
| | $SiO_2/Al_2O_3$ | | | | | | | | | | | |
| | 23 | 23 | 23 | 23 | 50 | 50 | 50 | 50 | 80 | 80 | 80 | 80 |
| | Li (mass %) | | | | | | | | | | | |
| | 0 | 0.14 | 0.35 | 0.69 | 0 | 0.14 | 0.35 | 0.69 | 0 | 0.14 | 0.35 | 0.69 |
| | $H_2$ (mL/min) | | | | | | | | | | | |
| | 74 | 74 | 74 | 74 | 74 | 74 | 74 | 74 | 74 | 74 | 74 | 74 |
| | $N_2$ (mL/min) | | | | | | | | | | | |
| | 0 | 0 | 0 | 0 | 0 | 0 | 0 | 0 | 0 | 0 | 0 | 0 |
| | conversion, % | | | | | | | | | | | |
| | 99 | 99.6 | 97.6 | 84.8 | 99.3 | 98.1 | 94.9 | 86.8 | 98.0 | 89.5 | 75.1 | 70.9 |
| | Product Distribution (moles per 100 moles) | | | | | | | | | | | |
| Butanes | 1.0 | 0.4 | 2.4 | 15.2 | 0.7 | 1.9 | 5.1 | 13.2 | 2.0 | 10.5 | 24.9 | 29.1 |
| Butenes | 1.2 | 0.9 | 1.6 | 3.3 | 1.3 | 1.9 | 2.6 | 3.5 | 1.8 | 3.6 | 4.5 | 4.5 |
| Ethylene | 22.5 | 25.5 | 27.9 | 22.0 | 28.3 | 29.9 | 25.8 | 18.2 | 26.0 | 24.1 | 19.0 | 16.8 |
| Propylene | 10.5 | 9.1 | 14.6 | 20.1 | 12.0 | 15.8 | 17.9 | 18.1 | 14.7 | 20.0 | 15.7 | 19.4 |
| Propane | 4.6 | 4.0 | 4.6 | 3.7 | 4.7 | 5.0 | 5.0 | 2.8 | 4.3 | 4.4 | 2.9 | 2.7 |
| Ethane | 11.6 | 14.0 | 12.9 | 10.1 | 13.0 | 13.7 | 13.4 | 8.5 | 12.6 | 13.2 | 14.1 | 10.1 |
| Methane | 16.3 | 19.1 | 17.5 | 14.5 | 17.6 | 17.8 | 16.6 | 11.4 | 15.9 | 16.4 | 12.7 | 13.4 |
| iso-Olefins | 0.6 | 0.5 | 0.8 | 1.8 | 0.6 | 0.9 | 1.2 | 1.7 | 0.8 | 1.8 | 2.4 | 2.2 |
| Aromatics | 31.7 | 26.4 | 17.6 | 9.3 | 21.7 | 13.2 | 12.4 | 22.7 | 21.7 | 6.1 | 3.8 | 1.7 |
| (E + B + P) | 34.0 | 35.0 | 44.9 | 57.3 | 41.0 | 47.6 | 48.8 | 49.5 | 42.7 | 54.6 | 59.6 | 65.3 |
| (E + B + P)/A | 1.1 | 1.3 | 2.6 | 6.2 | 1.9 | 3.6 | 3.9 | 2.2 | 2.0 | 9.0 | 15.7 | 38.4 |
| Vs. Control | 1 | 1.2 | 2.3 | 4.5 | 1 | 1.9 | 1.9 | 0.9 | 1 | 4.0 | 5.3 | 12.2 |

*Comparative Catalyst

TABLE 8

Activity of butane cracking over catalysts A-L at H$_2$/N$_2$ flow-rate ratio of 50:23

| | Catalyst | | | | | | | | | | | |
|---|---|---|---|---|---|---|---|---|---|---|---|---|
| | A* | B | C | D | E* | F | G | H | I* | J | K | L |
| SiO$_2$/Al$_2$O$_3$ | 23 | 23 | 23 | 23 | 50 | 50 | 50 | 50 | 80 | 80 | 80 | 80 |
| Li (mass %) | 0 | 0.14 | 0.35 | 0.69 | 0 | 0.14 | 0.35 | 0.69 | 0 | 0.14 | 0.35 | 0.69 |
| H$_2$ (mL/min) | 50 | 50 | 50 | 50 | 50 | 50 | 50 | 50 | 50 | 50 | 50 | 50 |
| N$_2$ (mL/min) | 23 | 23 | 23 | 23 | 23 | 23 | 23 | 23 | 23 | 23 | 23 | 23 |
| conversion, % | 99 | 99.6 | 97.3 | 84.2 | 99.2 | 98.4 | 94.4 | 84.2 | 97.6 | 90.2 | 81 | 71.3 |
| Product Distribution (moles per 100 moles) | | | | | | | | | | | | |
| Butanes | 1.0 | 0.4 | 2.7 | 15.8 | 0.8 | 1.6 | 5.6 | 15.8 | 2.4 | 9.8 | 19.0 | 28.7 |
| Butenes | 1.3 | 1.0 | 1.8 | 3.7 | 1.3 | 1.8 | 2.5 | 4.3 | 2.1 | 3.7 | 4.5 | 5.1 |
| Ethylene | 22.5 | 22.7 | 24.1 | 20.1 | 21.5 | 27.2 | 28.1 | 21.4 | 27.2 | 23.8 | 21.1 | 17.1 |
| Propylene | 10.9 | 8.9 | 13.8 | 19.2 | 10.7 | 14.8 | 20.1 | 21.7 | 16.3 | 20.7 | 22.0 | 20.9 |
| Propane | 4.1 | 3.1 | 3.4 | 2.8 | 3.8 | 3.8 | 3.7 | 2.8 | 3.7 | 3.5 | 2.8 | 2.2 |
| Ethane | 9.3 | 11.0 | 10.0 | 8.1 | 9.7 | 11.0 | 10.1 | 8.8 | 11.4 | 10.7 | 9.5 | 8.4 |
| Methane | 15.1 | 15.3 | 14.0 | 12.3 | 13.6 | 14.3 | 13.5 | 12.3 | 14.6 | 13.4 | 12.3 | 11.2 |
| iso-Olefins | 0.6 | 0.5 | 0.8 | 1.8 | 0.6 | 0.9 | 1.4 | 2.0 | 1.0 | 1.8 | 2.2 | 2.5 |
| Aromatics | 33.9 | 37.2 | 29.4 | 16.3 | 38.1 | 24.7 | 15.1 | 10.9 | 21.2 | 12.5 | 6.6 | 4.0 |
| (E + B + P) | 34.4 | 32.0 | 40.6 | 55.1 | 33.0 | 43.6 | 53.8 | 58.9 | 45.9 | 54.3 | 62.1 | 66.7 |
| (E + B + P)/A | 1.0 | 0.9 | 1.4 | 3.4 | 0.9 | 1.8 | 3.6 | 5.4 | 2.2 | 4.3 | 9.4 | 16.7 |
| Vs. Control | 1 | 0.9 | 1.3 | 2.6 | 1 | 2.0 | 3.8 | 4.9 | 1 | 1.8 | 3.4 | 5.0 |

*Comparative Catalyst

TABLE 9

Activity of butane cracking over catalysts A-L at H$_2$/N$_2$ flow-rate ratio of 30:43

| | Catalyst | | | | | | | | | | | |
|---|---|---|---|---|---|---|---|---|---|---|---|---|
| | A* | B | C | D | E* | F | G | H | I* | J | K | L |
| SiO$_2$/Al$_2$O$_3$ | 23 | 23 | 23 | 23 | 50 | 50 | 50 | 50 | 80 | 80 | 80 | 80 |
| Li (mass %) | 0 | 0.14 | 0.35 | 0.69 | 0 | 0.14 | 0.35 | 0.69 | 0 | 0.14 | 0.35 | 0.69 |
| H$_2$ (mL/min) | 30 | 30 | 30 | 30 | 30 | 30 | 30 | 30 | 30 | 30 | 30 | 30 |
| N$_2$ (mL/min) | 43 | 43 | 43 | 43 | 43 | 43 | 43 | 43 | 43 | 43 | 43 | 43 |
| conversion, % | 99 | 99.6 | 96.8 | 83.7 | 99.1 | 98.5 | 94.6 | 84.1 | 96.2 | 89.7 | 80.5 | 70.1 |
| Product Distribution (moles per 100 moles) | | | | | | | | | | | | |
| Butanes | 1.0 | 0.4 | 3.2 | 16.3 | 0.9 | 1.5 | 5.4 | 15.9 | 3.8 | 10.3 | 19.5 | 29.9 |
| Butenes | 1.4 | 1.0 | 1.8 | 3.9 | 1.4 | 1.8 | 2.9 | 4.3 | 2.6 | 3.9 | 4.8 | 5.4 |
| Ethylene | 24.1 | 20.7 | 22.3 | 19.0 | 20.4 | 26.1 | 25.7 | 20.7 | 27.9 | 23.0 | 20.4 | 16.6 |
| Propylene | 11.5 | 8.6 | 13.6 | 18.6 | 10.7 | 14.6 | 19.0 | 21.5 | 18.5 | 21.1 | 22.3 | 21.1 |
| Propane | 3.3 | 2.5 | 2.6 | 2.2 | 3.5 | 3.1 | 2.9 | 2.3 | 3.1 | 2.8 | 2.4 | 1.9 |
| Ethane | 9.3 | 9.3 | 8.4 | 6.8 | 8.7 | 9.5 | 9.3 | 7.7 | 10.4 | 9.1 | 8.3 | 7.2 |
| Methane | 13.9 | 13.1 | 12.3 | 10.9 | 12.3 | 12.6 | 12.5 | 11.1 | 13.6 | 11.5 | 11.0 | 9.9 |
| iso-Olefins | 0.6 | 0.5 | 0.9 | 1.9 | 0.7 | 0.9 | 1.4 | 2.1 | 1.2 | 1.9 | 2.3 | 2.6 |
| Aromatics | 34.9 | 43.9 | 34.9 | 20.5 | 41.4 | 29.9 | 20.8 | 14.2 | 18.9 | 16.2 | 8.9 | 5.4 |
| (E + B + P) | 36.6 | 29.7 | 39.1 | 53.9 | 32.0 | 42.2 | 50.1 | 58.1 | 50.2 | 54.4 | 62.2 | 67.6 |
| (E + B + P)/A | 1.0 | 0.7 | 1.1 | 2.6 | 0.8 | 1.4 | 2.4 | 4.1 | 2.7 | 3.4 | 7.0 | 12.5 |
| Vs. Control | 1 | 0.7 | 1.0 | 1.9 | 1 | 1.8 | 2.9 | 4.2 | 1 | 1.1 | 2.1 | 3.1 |

*Comparative Catalyst

TABLE 10

Activity of butane cracking over catalysts A-L at $H_2/N_2$ flow-rate ratio of 10:63

| | Catalyst | | | | | | | | | | | |
|---|---|---|---|---|---|---|---|---|---|---|---|---|
| | A* | B | C | D | E* | F | G | H | I* | J | K | L |
| $SiO_2/Al_2O_3$ | 23 | 23 | 23 | 23 | 50 | 50 | 50 | 50 | 80 | 80 | 80 | 80 |
| Li (mass %) | 0 | 0.14 | 0.35 | 0.69 | 0 | 0.14 | 0.35 | 0.69 | 0 | 0.14 | 0.35 | 0.69 |
| $H_2$ (mL/min) | 10 | 10 | 10 | 10 | 10 | 10 | 10 | 10 | 10 | 10 | 10 | 10 |
| $N_2$ (mL/min) | 63 | 63 | 63 | 63 | 63 | 63 | 63 | 63 | 63 | 63 | 63 | 63 |
| conversion, % | 99.4 | 99.6 | 97.2 | 85.5 | 99.5 | 98.8 | 95.2 | 85.9 | 95.7 | 89.3 | 80.9 | 72 |
| Product Distribution (moles per 100 moles) | | | | | | | | | | | | |
| Butanes | 0.6 | 0.4 | 2.8 | 14.5 | 0.5 | 1.2 | 4.8 | 14.1 | 4.3 | 10.7 | 19.1 | 29.6 |
| Butenes | 1.1 | 0.8 | 1.7 | 3.9 | 1.0 | 1.6 | 2.7 | 4.2 | 2.6 | 4.0 | 5.1 | 6.0 |
| Ethylene | 22.0 | 17.7 | 20.5 | 19.0 | 18.2 | 24.0 | 24.2 | 20.9 | 26.4 | 21.9 | 19.8 | 16.1 |
| Propylene | 9.8 | 7.3 | 12.3 | 17.5 | 8.8 | 13.2 | 17.6 | 20.7 | 18.5 | 21.0 | 22.6 | 21.2 |
| Propane | 2.6 | 1.8 | 2.1 | 1.7 | 2.9 | 2.5 | 2.4 | 2.1 | 2.7 | 2.6 | 2.5 | 2.0 |
| Ethane | 6.1 | 7.3 | 6.7 | 5.5 | 7.0 | 8.0 | 7.9 | 6.7 | 9.1 | 7.9 | 7.1 | 6.1 |
| Methane | 12.7 | 11.2 | 11.0 | 9.8 | 11.4 | 11.2 | 11.1 | 10.1 | 12.3 | 10.2 | 9.9 | 8.8 |
| iso-Olefins | 0.5 | 0.4 | 0.8 | 1.9 | 0.5 | 0.8 | 1.3 | 2.1 | 1.3 | 1.9 | 2.5 | 2.8 |
| Aromatics | 43.2 | 53.2 | 42.2 | 26.2 | 49.8 | 37.6 | 27.9 | 19.2 | 22.8 | 19.8 | 11.3 | 7.4 |
| (E + B + P) | 32.4 | 25.4 | 35.6 | 51.0 | 27.5 | 38.4 | 46.6 | 55.7 | 49.2 | 53.6 | 61.5 | 66.9 |
| (E + B + P)/A | 0.8 | 0.5 | 0.8 | 1.9 | 0.6 | 1.0 | 1.7 | 2.9 | 2.2 | 2.7 | 5.4 | 9.0 |
| Vs. Control | 1 | 0.6 | 1.1 | 2.0 | 1 | 1.8 | 2.8 | 4.2 | 1 | 1.1 | 2.0 | 2.8 |

*Comparative Catalyst

TABLE 11

Activity of butane cracking over catalysts A-L at $H_2/N_2$ flow-rate ratio of 2:72

| | Catalyst | | | | | | | | | | | |
|---|---|---|---|---|---|---|---|---|---|---|---|---|
| | A* | B | C | D | E* | F | G | H | I* | J | K | L |
| $SiO_2/Al_2O_3$ | 23 | 23 | 23 | 23 | 50 | 50 | 50 | 50 | 80 | 80 | 80 | 80 |
| Li (mass %) | 0 | 0.14 | 0.35 | 0.69 | 0 | 0.14 | 0.35 | 0.69 | 0 | 0.14 | 0.35 | 0.69 |
| $H_2$ (mL/min) | 2 | 2 | 2 | 2 | 2 | 2 | 2 | 2 | 2 | 2 | 2 | 2 |
| $N_2$ (mL/min) | 72 | 72 | 72 | 72 | 72 | 72 | 72 | 72 | 72 | 72 | 72 | 72 |
| conversion, % | 99.8 | 99.7 | 98.3 | 90.8 | 99.8 | 99.3 | 96.6 | 90.2 | 95.8 | 89.5 | 81.7 | 72 |
| Product Distribution (moles per 100 moles) | | | | | | | | | | | | |
| Butanes | 0.2 | 0.3 | 1.7 | 9.2 | 0.2 | 0.7 | 3.4 | 9.8 | 4.2 | 10.5 | 18.3 | 28.0 |
| Butenes | 0.7 | 0.6 | 1.2 | 3.2 | 0.6 | 1.2 | 2.1 | 3.6 | 2.4 | 3.8 | 5.2 | 6.4 |
| Ethylene | 19.3 | 15.1 | 18.2 | 19.7 | 16.2 | 21.2 | 22.7 | 21.4 | 24.8 | 20.5 | 18.8 | 15.8 |
| Propylene | 7.1 | 5.8 | 9.6 | 15.3 | 6.5 | 10.4 | 15.0 | 18.4 | 17.2 | 19.6 | 21.7 | 21.0 |
| Propane | 2.4 | 1.7 | 1.8 | 1.6 | 2.5 | 2.4 | 2.3 | 2.1 | 2.8 | 2.6 | 2.7 | 2.3 |
| Ethane | 5.4 | 5.8 | 5.4 | 4.8 | 5.3 | 6.7 | 6.7 | 5.9 | 8.1 | 7.0 | 6.3 | 5.4 |
| Methane | 12.9 | 10.2 | 10.1 | 9.4 | 11.1 | 10.7 | 10.5 | 9.7 | 11.9 | 9.6 | 9.3 | 8.4 |
| iso-Olefins | 0.3 | 0.3 | 0.6 | 1.5 | 0.3 | 0.6 | 1.0 | 1.7 | 1.1 | 1.8 | 2.5 | 3.0 |
| Aromatics | 51.1 | 60.3 | 51.5 | 35.3 | 57.3 | 46.4 | 36.2 | 27.4 | 27.5 | 24.5 | 15.2 | 9.6 |
| (E + B + P) | 26.6 | 21.2 | 29.5 | 44.2 | 22.9 | 32.3 | 41.1 | 49.6 | 46.2 | 50.6 | 58.8 | 64.8 |
| (E + B + P)/A | 0.5 | 0.4 | 0.6 | 1.3 | 0.4 | 0.7 | 1.1 | 1.8 | 1.7 | 2.1 | 3.9 | 6.8 |
| Vs. Control | 1 | 0.7 | 1.1 | 2.0 | 1 | 1.7 | 2.7 | 3.9 | 1 | 1.1 | 1.9 | 2.8 |

*Comparative Catalyst

In general, butane conversion decreases with increasing Li content in the zeolite, under all of the carrier gas compositions. On the other hand, ethylene yield was found to be sensitive to the composition of the carrier gas where it decreased with decreasing hydrogen content in the feed stream. The yield of aromatics formed also decreased with increasing Li content in the zeolite. Similarly, yields of methane, ethane, and propane decreased with increasing Li content in the zeolite and amount of hydrogen in the feed stream. Without intent to be bound by theory, the decrease may be a result of a decrease in the activity of the hydride-transfer side reaction that may also be the reason behind the observed increase of propylene yield with increasing Li-content in the zeolite. A maximum of 48.2% combined yield of ethylene plus propylene was obtained over catalyst G when used a carrier gas with hydrogen to nitrogen flow ratio of 50:30 mL/minute.

Thus, by the methods for cracking a hydrocarbon feed stream as described in this disclosure, the addition of small amounts of lithium to ZSM-5 zeolite favorably increased catalyst activity, selectivity, and stability compared to ZSM-5 zeolites with no added lithium. In particular, when small amounts of lithium were added to ZSM-5 zeolites with silica to alumina ratios of 23, 50 or 80, the selectivity for propylene formation significantly increased while selectivity for the formation of aromatics and hydride-transfer reaction products such as methane, ethane, and propane decreased. Further, by the methods described in this disclosure, the ZSM-5 catalysts were stabilized against deactivation by coke formation, which in turn enabled the operation of the butane cracking process in a fixed-bed based reactor continuously for over 12 hours.

Items Listing

Embodiments of the present disclosure include at least following items, which are not intended to limit the scope of the disclosure as a whole or the appended claims.

Item 1: A method for cracking a hydrocarbon feed stream, the method comprising contacting the hydrocarbon feed stream with a catalyst system in a catalytic cracking unit having a flowing gas stream to obtain a cracking product containing light olefins, wherein: the catalyst system comprises a pentasil zeolite; the pentasil zeolite comprises from 0.01% to 5% by mass lithium atoms, as calculated on an oxide basis, based on the total mass of the pentasil zeolite; and the flowing gas stream comprises hydrogen.

Item 2: The method of Item 1, wherein the pentasil zeolite comprises from 0.01% to 2% by mass lithium atoms, as calculated on an oxide basis, based on the total mass of the pentasil zeolite.

Item 3: The method of any one of Items 1 to 2, wherein the pentasil zeolite comprises from 0.1% to 1% by mass lithium atoms, as calculated on an oxide basis, based on the total mass of the pentasil zeolite.

Item 4: The method of any one of Items 1 to 3, wherein the pentasil zeolite is ZSM-5.

Item 5: The method of any one of Items 1 to 4, wherein the pentasil zeolite has a silica-to-alumina ratio from 5:1 to 200:1.

Item 6: The method of any one of Items 1 to 5, wherein the pentasil zeolite has a silica-to-alumina ratio from 20:1 to 100:1.

Item 7: The method of any one of Items 1 to 6, wherein the hydrocarbon feed stream comprises $C_4$-$C_6$ saturated hydrocarbons.

Item 8: The method of any one of Items 1 to 7, wherein the light olefins comprise ethylene, propylene, and butylenes.

Item 9: The method of any one of Items 1 to 8, wherein the flowing gas stream further comprises a carrier gas.

Item 10: The method of Item 9, wherein the carrier gas comprises steam, nitrogen, argon, or combinations thereof.

Item 11: The method of any one of Items 1 to 10, wherein the flowing gas stream comprises hydrogen and nitrogen at a volumetric flow-rate ratio $H_2:N_2$ from 1000:1 to 1:50.

Item 12: The method of any one of Items 1 to 11, wherein the catalytic cracking unit is a fixed-bed reactor.

Item 13: The method of any one of Items 1 to 12, wherein: the contacting occurs at a reaction temperature from 500° C. to 650° C., at a reaction pressure from 0.01 bar to 10 bar, with a residence or contact time from 0.1 seconds to 60 seconds, with a weight hour space velocity from 0.5 $h^{-1}$ to 4 $h^{-1}$, and with a catalyst to oil ratio from about 1:4 to 2:1.

Item 14: The method of any one of Items 1 to 13, further comprising: separating from the cracking product a first liquid stream including hydrocarbons with four or fewer hydrogen atoms, a second stream including saturated hydrocarbons, and a third stream including unsaturated hydrocarbons; and recycling the third stream to the catalytic cracking unit.

Item 15: The method of any one of Items 1 to 14, further comprising: recovering hydrogen from the cracking product; and recycling the recovered hydrogen to the catalytic cracking unit.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

What is claimed is:

1. A method for cracking a hydrocarbon feed stream, the method comprising
contacting the hydrocarbon feed stream with a catalyst system in a catalytic cracking unit having a flowing gas stream to obtain a cracking product containing light olefins,
wherein:
the catalyst system comprises a pentasil zeolite;
the pentasil zeolite consists of ZSM-5 and from 0.01% to 5% by mass lithium atoms, as calculated on an oxide basis, based on the total mass of the pentasil zeolite; the hydrocarbon feed stream comprises $C_4$-$C_6$ saturated hydrocarbons;
the flowing gas stream comprises hydrogen; and
the pentasil zeolite has a silica-to-alumina ratio from 20:1 to 100:1.

2. The method of claim 1, wherein the pentasil zeolite comprises from 0.01% to 2% by mass lithium atoms, as calculated on an oxide basis, based on the total mass of the pentasil zeolite.

3. The method of claim 1, wherein the pentasil zeolite comprises from 0.1% to 1% by mass lithium atoms, as calculated on an oxide basis, based on the total mass of the pentasil zeolite.

4. The method of claim 1, wherein the light olefins comprise ethylene, propylene, and butylenes.

5. The method of claim 1, wherein the flowing gas stream further comprises a carrier gas.

6. The method of claim 5, wherein the carrier gas comprises steam, nitrogen, argon, or combinations thereof.

7. The method of claim 1, wherein the flowing gas stream comprises hydrogen and nitrogen at a volumetric flow-rate ratio $H_2:N_2$ from 1000:1 to 1:50.

8. The method of claim 1, wherein the catalytic cracking unit is a fixed-bed reactor.

9. The method of claim 1, wherein:
the contacting occurs at a reaction temperature from 500° C. to 650° C., at a reaction pressure from 0.01 bar to 10 bar, with a residence or contact time from 0.1 seconds to 60 seconds, with a weight hour space velocity from 0.5 $h^{-1}$ to 4 $h^{-1}$, and with a catalyst to oil ratio from 1:4 to 2:1.

10. The method of claim 1, further comprising:
separating from the cracking product a first stream including hydrocarbons with four or fewer carbon atoms, a second stream including saturated hydrocarbons, and a third stream including $C_4$-$C_{12}$ unsaturated hydrocarbons; and
recycling the second and third streams to the catalytic cracking unit.

11. The method of claim 1, further comprising:
recovering hydrogen from the cracking product; and
recycling the recovered hydrogen to the catalytic cracking unit.

12. The method of claim 1, wherein the flowing gas stream comprises hydrogen and nitrogen at a volumetric flow-rate ratio $H_2:N_2$ from 50:23 to 2:72.

13. The method of claim 1, wherein:
the pentasil zeolite comprises from 0.1% to 1% by mass lithium atoms, as calculated on an oxide basis, based on the total mass of the pentasil zeolite;
the pentasil zeolite is ZSM-5; and
the flowing gas stream comprises hydrogen and nitrogen at a volumetric flow-rate ratio $H_2:N_2$ from 50:23 to 2:72.

14. The method of claim 1, wherein the catalyst system consists of the pentasil zeolite and the lithium atoms.

15. The method of claim 1, wherein the flowing gas stream comprises hydrogen and nitrogen at a volumetric flow-rate ratio $H_2:N_2$ from 30:43 to 2:72.

16. The method of claim 1, wherein the flowing gas stream comprises hydrogen and nitrogen at a volumetric flow-rate ratio $H_2:N_2$ from 30:43 to 10:63.

* * * * *